United States Patent [19]

Yamazaki

[11] 4,134,411
[45] Jan. 16, 1979

[54] ACIDIC TWO-BATH TYPE COMPOSITION FOR PERMANENT WAVING OF HAIR AND FOR TREATMENT OF HAIR AND SCALP

[76] Inventor: Ikue Yamazaki, 32-10 Hakusan-1-chome, Bunkyo-ku, Tokyo, Japan

[21] Appl. No.: 656,207

[22] Filed: Feb. 9, 1976

[30] Foreign Application Priority Data

Sep. 5, 1975 [JP] Japan .................. 50-107911

[51] Int. Cl.$^2$ .................. A45D 7/02; A45D 7/06
[52] U.S. Cl. .................. 132/7; 81/127.51; 424/71; 424/72
[58] Field of Search .................. 424/71, 72; 132/7; 8/127.51

[56] References Cited

U.S. PATENT DOCUMENTS

| 3,847,165 | 11/1974 | Patel et al. | 132/7 |
| 3,849,576 | 11/1974 | Kalopissis | 424/71 X |
| 3,865,930 | 2/1975 | Abegg et al. | 424/72 |

FOREIGN PATENT DOCUMENTS

| 101019 | 2/1965 | Denmark | 424/71 |
| 1346564 | 11/1963 | France | 424/71 |
| 1537672 | 7/1968 | France | 424/71 |

Primary Examiner—Jerome D. Goldberg
Assistant Examiner—Vera C. Clarke
Attorney, Agent, or Firm—Oblon, Fisher, Spivak, McClelland & Maier

[57] ABSTRACT

An acidic two-bath type composition for the permanent waving of the human hair as well as for the treatment of the human hair and scalp, which consists of an aqueous reducing agent solution (the first bath) containing 3 to 10% by weight of at least one mercaptan acid such as, for example, thioglycolic acid or thiolactic acid and an aqueous oxidizing agent solution (the second bath) containing 1 to 10% by weight of sodium bromate, potassium bromate, or hydrogen peroxide, said reducing agent solution having a pH adjusted with a base to a value 0.1 to 2.0 lower than the isoelectric point of the hair or scalp and said oxidizing agent solution having a pH adjusted with an acid to a value 0.1 to 2.0 lower than the pH of said reducing agent solution but not more than 3.0 lower than the said isoelectric point. Although this composition can be used in a customary manner, it is preferable to apply the oxidizing agent solution having an initial pH 0.1 to 2.0 lower than the pH of said reducing agent solution but not more than 3.0 lower than the isoelectric point, and then, during the application, further adjusting the pH to a value lower than the initial pH. This composition is suitable for imparting a permanent wave to the human hair and for treating the human scalp and hair to enhance the physiological activity of the scalp and hair. The permanent wave of the hair treated with this acidic two-bath type composition is very stable and the scalp and hair treated with the composition is markedly improved in physiological activity.

5 Claims, No Drawings

ACIDIC TWO-BATH TYPE COMPOSITION FOR PERMANENT WAVING OF HAIR AND FOR TREATMENT OF HAIR AND SCALP

This invention relates to an acidic two-bath type composition for the permanent waving of human hair and for the treatment of human hair and scalp and, more particularly, to an acidic two-bath type composition for the permanent waving of human hair and for the treatment of human hair and scalp consisting of an acidic aqueous reducing agent solution (the first bath) and an acidic aqueous oxidizing agent solution (the second bath).

The present inventor disclosed in French Pat. No. 1,537,672 and Japanese Patent Publication No. 44,862/73 a three-bath type composition for the permanent waving of human hair comprising an acidic aqueous reducing agent solution, an acidic aqueous oxidizing agent solution, and an alkaline aqueous solution. The inventor's further investigations revealed surprisingly and unexpectedly that the treatment with the alkaline aqueous solution (the third bath) of said three-bath type composition is rather harmful to the human hair and scalp for the following reason: The human hair and scalp treated with the acidic reducing agent solution and the acidic oxidizing agent solution are in an acidic state, the pH being 1.5 to 2.0 lower than the isoelectric point of the human hair and scalp, and hence, are physiologically active. When the hair and scalp in said state are treated with the alkaline third bath, the pH of the solution contacting the hair and scalp, in some cases, becomes substantially equal to the isoelectric point of the hair and scalp, causing coagulation of the protein which results in extreme diseccation of the hair and scalp. It has also been found that the hair becomes too stiff to be combed and the scalp becomes extremely dandruffy. In most cases, the pH of the third bath is on the alkaline side beyond the isoelectric point of the hair and scalp, causing swelling of the hair and scalp, and results in a decrease in strength and suppleness of the hair.

The present inventor has found surprisingly that when the human hair and scalp are treated with an acidic reducing agent bath followed by treatment with an acidic oxidizing agent bath without the subsequent treatment with the alkaline bath, the imparted permanent wave is more stable, the physiological activity of the scalp is more enhanced, and the hair is more improved in suppleness, strength, and resilience than when the subsequent treatment with the third alkaline bath is carried out.

On continued investigations, it has further been found that in a customary acid process for the permanent waving, when the hair and scalp are repeatedly treated with a second bath, i.e., an acidic aqueous oxidizing agent solution, while circulating the bath, the pH of the bath is shifted toward the alkaline side with the lapse of time owing to contamination with various waste matters from the scalp; for instance, the initial pH of 4.0 of the aqueous oxidizing agent solution increased to 4.2 to 4.8 after 2 or 3 minutes and to 5.5 to 6.0 after 5 to 10 minutes, approximating to the isoelectric point of protein (the isoelectric point being dependent on the human race, sex, and age). As is well known, an aqueous oxidizing agent solution in this range of pH is unable to exhibit its oxidizing effect in treating human hair or scalp, while the protein tends to coagulate or become physiologically least active at a pH corresponding to the isoelectric point. It has been thus found necessary to control the pH of the second bath, throughout the course of treating the hair or scalp, so as not to become greater than the pH of the reducing agent bath (the first bath).

The present inventor has further found that more favorable results are obtained when the pH of the reducing bath is 0.1 to 2.0 lower than the isoelectric point of protein, and the pH of the oxidizing agent bath is always lower than the pH of the reducing agent bath during the treatment with the oxidizing agent bath.

An object of this invention is to provide an acidic composition for the permanent waving of human hair, which will not cause coagulation of the protein.

Another object of this invention is to provide an acidic two-bath type composition for the permanent waving of human hair.

A further object of this invention is to provide an acidic two-bath type composition for the treatment of human hair and scalp to increase the physiological activity thereof for the purpose of controlling beauty and health.

A still further object of this invention is to provide a method for the treatment of the human hair and scalp for the purpose of imparting a stable permanent wave to the hair.

Other objects and advantages of this invention will become apparent from the following description.

According to this invention, there is provided an acidic two-bath type composition for the permanent waving of human hair as well as for the treatment of the human hair and scalp, which consists of an aqueous reducing agent solution (the first bath) containing 3 to 10% by weight of at least one mercaptan acid and an aqueous oxidizing agent solution (the second bath) containing 1 to 10% by weight of potassium bromate, sodium bromate, or hydrogen peroxide, said reducing agent solution having a pH adjusted with a base to a value 0.1 to 2.0 lower, preferably 0.1 to 1.0 lower, than the isoelectric point of the human hair or scalp, and said oxidizing agent solution having a pH adjusted with an acid to a value 0.1 to 2.0 lower than the pH of said reducing agent solution but not more than 3.0 lower than the said isoelectric point.

The mercaptan acid used as the reducing agent in accordance with this invention includes, for example, thioglycolic acid, thiolactic acid, and the like. These mercaptan acids may be used alone or in combination of two or more. The reducing agent is dissolved in a suitable amount of water so that the concentration may be in the range from 3 to 10% by weight. Within the said range, the concentration is properly adjusted according to the state of the hair and/or scalp. The pH of the aqueous reducing agent solution thus obtained is adjusted to a value 0.1 to 2.0 lower, preferably less than 1.0 lower, more preferably 0.1 to 0.5 lower, than the isoelectric point of the hair by the addition of at least one base selected from the group consisting of inorganic bases such as sodium hydroxide, potassium hydroxide, sodium carbonate, potassium carbonate and the like; amino-alcohols such as monoethanolamine, triethanolamine and the like; and ammonia. The reducing agent solution is used at 20° to 40° C. Some hair is treated with a lower concentration of the reducing agent solution, and in this case, it is sometime difficult to impart permanent wave to the hair. In such a case, the treatment is effected at higher temperatures to enable the permanent waving.

The isoelectric point of the human hair is in the neighborhood of 5.0, generally in the range from 4.5 to 6.0 depending on the human race, age, and sex. Accordingly, if the isoelectric point is 5.0, the pH of an aqueous reducing agent solution is adjusted to a value within the range from 4.9 to 3.0 depending upon the state of hair and/or scalp. If the pH of the reducing agent bath is below the lower limit of the said range, the activity of the oxidizing agent bath will not sufficiently be manifested. To the aqueous reducing agent solution thus prepared may be added, if necessary, any of the usual auxiliary agents such as glycerol; a nonionic surface active agent, for example, polyoxyethylene nonyl phenyl ether, polyoxyethylene octyl ether or the like; liquid paraffin or lanolin. An antioxidant such as thiourea can also be added to keep the reducing agent bath from degeneration in activity and also to keep the pH from change. The amount of the auxiliary agent to be added is similar to that in a conventional system, that is, 5 to 15% by weight for the glycerol and 0.01 to 0.3% by weight for the nonionic surface active agent.

The oxidizing agents used in accordance with this invention are sodium bromate, potassium bromate, and hydrogen peroxide. These are used alone or in admixture of two or more. Although the concentration of an oxidizing agent in the aqueous solution is variable depending on pH, it is generally 1 to 10%, desirable 1 to 5%, more desirably 2 to 3%, by weight. If the pH is lower, the concentration is preferably lower within the said range. A higher concentration is usually preferred for the permanent waving of the hair of Europeans. The pH of the aqueous oxidizing agent solution is adjusted to a value 0.1 to 2.0 lower than the pH of the reducing agent solution by use of an organic acid such as citric acid, tartaric acid, succinic acid, oxalic acid or the like; an inorganic acid such as hydrochloric acid, sulfuric acid, nitric acid or the like; or a mixture of two or more of these acids. If any case, care must be taken so as not to allow the pH of the oxidizing solution to become more than 3.0, preferably more than 1.5, lower than the isoelectric point. The adjustment of the pH within the said range is necessary for the enhancement of oxidizing activity of the oxidizing agent bath and for the effective elimination of waste matter from skin. Moreover, the said pH adjustment is also necessary for fixing and stabilizing the curls of hair treated with the reducing agent solution without impairing the hair and rather for increasing the strength of the hair. The oxidizing agent solution, the pH of which has been changed during the treatment, is adjusted to the desired pH with the above-mentioned acid or its aqueous solution for preparing the oxidizing agent solution. In order to carry out the oxidation and the elimination of waste matter, it is preferable to adjust the initial pH of the aqueous oxidizing agent solution to a value 0.1 to 1.5, preferably 0.3 to 0.5 lower than the pH of the reducing agent solution, and, after the treatment with the oxidizing agent solution has been effected for a suitable period of time (generally 5 to 10 minutes), to adjust again the pH with the above-mentioned acid or its aqueous solution to a value lower than the initial pH and continue the treatment, while restoring the initial concentration of the oxidizing agent by replenishment. Alternatively, the oxidation treatment can be carried out in the following way: the oxidizing agent bath is divided into two aqueous oxidizing agent solutions A and B, the oxidizing agent solution A containing 0.5 to 3% by weight of the oxidizing agent and having a pH adjusted to a value 0.1 to 1.5, preferably 0.3 to 0.5, lower than the pH of the reducing agent bath, provided that the pH of the oxidizing agent solution A is not more than 2.7 lower than the isoelectric point, and the oxidizing agent solution B containing 1 to 5% by weight of the oxidizing agent and having a pH adjusted to a value 0.1 to 2.0, preferably 0.3 to 0.5, lower than the pH of the oxidizing agent solution A, provided that the pH of the oxidizing agent solution B is not more than 3.0 lower than the isoelectric point; the oxidation treatment is first conducted with the oxidizing agent solution A for a period of, for instance, 5 to 10 minutes, and thereafter with the oxidizing agent solution B. In this case, either of the oxidizing agent solutions A and B can be conveniently prepared by proper adjustment of concentration and pH from a stock oxidizing agent preparation with higher concentration within the range in accordance with this invention. As in the case of the conventional system in French Pat. No. 1,537,672, the present aqueous oxidizing agent solution can be incorporated with 0.1 to 0.4% by weight of glutamic acid to enhance the oxidizing activity and, if necessary, with suitable amounts of a hair-nourishment and a mineral ingredient.

By treating human hair with the present two-bath type composition as mentioned above, an excellent permanent wave effect is obtained, and by treating the human scalp with the present composition, the elimination of waste matter from the head skin is effectively achieved. Moreover, a similar treatment of a face and hands results in a promotion or recovery of health of skin and achieves the greatest purpose of makeup.

When the human scalp, or hand or foot skin is treated with the present composition, proteins and the like which are considered to be waste matters present in the body are discharged into the treating solution. The discharge of waste matters is considered to promote the metabolism through the skin and activate the physiological action, whereby the health of skin is increased, that is to say, beauty is maintained, and the health of the whole body is increased. Moreover, when the treatment with the present composition was applied to the hair or scalp of a lead-intoxicative person, lead was detected in the wasted composition. That is to say, the treatment of the skin with the present composition can be considered to become an effective means for discharging a poisonous substance such as lead besides the above mentioned waste proteins through physiological action.

The procedure for treating human hair and scalp with the present composition is as follows:

The first step

The hair is sufficiently impregnated with about 50 to 100 g per person (variable within the range depending upon the quantity of hair and the state of scalp) of the aqueous reducing agent solution (the pH of the solution is adjusted to, for example, 4.5 when the hair or scalp has an isoelectric point of 5.0) at 20° to 40° C. and allowed to stand under a suitable cover to keep the hair substantially from oxidation due to air for about 10 to 30 minutes, usually about 15 minutes. If necessary, it may be allowed to stand for a longer period. When the permanent waving is intended, immediately after the aqueous reducing agent solution has been applied, the hair wetted with the solution is wound on curling rods having a diameter corresponding to the intended wave style and the wound hair is covered and allowed to stand for a suitable period of time as mentioned above.

The second step

After the lapse of the above-mentioned time, there is applied to the hair and scalp a shower of the aqueous oxidizing agent solution having a pH adjusted to a value 0.1 to 2.0 lower, preferably 0.3 to 0.5 lower, than that of the reducing agent solution but not more than 3.0 lower than the isoelectric point (for example, a pH of 4.6 to 2.0), the volume of said oxidizing agent solution being 2-3 times the volume of the reducing agent solution, while circulating the oxidizing agent solution at a temperature of 20° to 40° C. By this treatment the hair and scalp are thoroughly impregnated with the aqueous oxidizing agent solution to replace the aqueous reducing agent solution therewith, and simultaneously eliminate dead cells, waste proteins and other waste matters of hair and scalp which have been released by the treatment with the reducing agent solution in the first step. The oxidation treatment restores the activity of the declined cells.

It is preferable that the aqueous oxidizing agent solution has a pH lower than and as near as possible to the isoelectric point in order to eliminate more effectively the waste matter, whereas it is necessary for the effective oxidation that the pH of the oxidizing agent solution be lower than that of the reducing agent solution. It is preferable, therefore, to carry out the oxidation treatment in the following way: The hair and scalp are treated with the aqueous oxidizing agent solution having an initial pH adjusted to a value 0.1 to 2.0 lower than the pH of the reducing agent solution usually for a period of 10 to 15 minutes. At the end of this period, the pH of the oxidizing agent solution is shifted toward the alkaline side owing to the waste matter including dead cells removed into the solution, and in some cases it becomes higher than the isoelectric point, and hence, the oxidization activity of the solution becomes substantially nil. In this case, the acid or its aqueous solution mentioned above is added to the solution to adjust the pH of the solution to a value lower than the initial pH but not more than 3.0 lower than the isoelectric point, and the concentration of the oxidizing agent is also replenished to 1 to 5% by weight. The oxidation treatment with this refreshed solution is continued for a further about 5 to 30 minutes. When the period of the treatment with the reducing agent bath is longer, the treatment with the oxidizing agent bath can be correspondingly prolonged to effect sufficient oxidation.

Alternatively, after the treatment with the reducing agent bath in the first step, the hair and scalp are first treated with 100 to 200 cc of the aforesaid aqueous oxidizing agent solution A (for example, pH is 4.2 and oxidizing agent content is 3% by weight) for a period of about 10 to 15 minutes and subsequently with the aqueous oxidizing agent solution B (for example, pH is 3.7 and oxidizing agent content is 3% by weight) for a period of 10 to 30 minutes. The use of the oxidizing agent solution B having a pH lower than that of the oxidizing agent solution A results in an increase of the oxidizing activity, whereby the oxidation action reaches the interior of the hair and scalp to enable a sufficient oxidation.

After completion of the treatment with the aqueous oxidizing agent solution, the hair and scalp are thoroughly washed with water and dried.

The permanent wave imparted by the process described above is very stable and durable, and the hair thus treated is improved in smoothness, suppleness, luster, and strength and is easily combed. Because of elimination of the horny dead cells from the scalp surface, the declined cells are restored and the physiological activity is increased. Further, the blood is purified and the scarf formation is greatly inhibited, resulting in an increase of skin respiration, and this is the most important for health and beauty care.

This invention is further explained below in more detail with reference to Examples, which are by way of illustration and not by way of limitation.

Example 1

| First bath (reducing agent bath) | |
|---|---|
| Thioglycolic acid | 7.0 g |
| Ammonia water (25% by weight) | 8.3 g |
| Glycerol | 10.0 g |
| Distilled water | 74.7 g |
| Total | 100.0 g |

These components were mixed to prepare an aqueous solution of the reducing agent. The pH of this solution was 4.5.

| Second bath (oxidizing agent bath) | |
|---|---|
| Sodium bromate | 5.0 g |
| Glutamic acid | 0.2 g |
| Distilled water | 194.8 g |
| Total | 200.0 g |

These components were mixed to prepare an aqueous solution, and the pH of the solution was adjusted to 4.0 by adding citric acid.

Separately, a 10% by weight aqueous solution of citric acid was prepared.

To the cleansed and dried hair (isoelectric point, 5.0) of a Japanese woman was applied 100 g of the above first bath (reducing agent bath) at room temperature. The tresses of the hair thus treated were rolled on curling rods and allowed to stand for 20 minutes, while protecting the hair from air.

200 g of the above second bath (oxidizing agent bath) was applied in the form of a shower to the hair and scalp while circulating the solution. After 5 minutes, the pH of the bath reached 4.7. Then, the above aqueous citric acid solution was added to the second bath to adjust the pH to 3.5. The resulting bath was applied again to the hair and scalp in the same manner as before for 15 minutes. Thereafter, the curling rods were removed and the hair and scalp were thoroughly washed with water, dried and finished.

The resulting permanent wave was much more stable than that obtained by the conventional alkaline method. There was no noticeable hair damage. As compared with the hair treated with a third bath comprising an aqueous alkaline solution, the hair treated with the present system was greatly improved in strength, luster, and suppleness, and became young.

Example 2

| Reducing agent bath (first bath) | |
|---|---|
| Thioglycolic acid | 5.0 g |
| Ammonia water (25% by weight) | 6.8 g |
| Glycerol | 10.0 g |
| Distilled water | 78.2 g |
| Total | 100.0 g |

These components were mixed to prepare an aqueous reducing agent solution. The pH thereof was 4.7.

| Oxidizing agent bath (second bath) Oxidizing agent solution A (second A bath) | |
| --- | --- |
| Sodium bromate | 6.0 g |
| Glutamic acid | 0.7 g |
| Nitric acid | 0.01 g |
| Distilled water to make 200 g. | |

These components were mixed to prepare an aqueous solution, and citric acid was added thereto to obtain an aqueous oxidizing agent solution having a pH of 4.3 (oxidizing agent solution A).

Oxidizing agent solution B (second B bath)

In the same manner as above, 200.0 g of an aqueous solution was prepared, and citric acid was added thereto to obtain an aqueous oxidizing agent solution having a pH of 3.9 (oxidizing agent preparation B).

To the cleansed and dried hair (isoelectric point, 5.1) of a Japanese woman was applied 100 g of the above reducing agent bath at room temperature, and the tresses of the hair thus treated were rolled on curling rods and allowed to stand for 30 minutes.

Subsequently, 200 g of the above oxidizing agent solution A was applied in the form of a shower to the hair and scalp for 15 minutes while circulating the solution, after which 200 g of the above aqueous reducing agent solution B was applied to the hair and scalp in the same manner for 15 minutes. The curling rods were then removed, and the hair and scalp were washed with water, dried and finished.

The thus obtained permanent wave showed substantially the same result as in Example 1.

COMPARATIVE EXAMPLE 1

The same procedure as in Example 2 was repeated, except that the pH of the reducing agent bath, the pH of the oxidizing agent solution A and the pH of the oxidizing agent solution B were adjusted to 4.5, 4.0 and 3.5, respectively.

In the same manner as in Example 2, white hair of a man 61 years old, said hair having an isoelectric point of 4.8 and having not been subjected to a treatment with an alkaline permanent waving agent and to hair-dyeing, was treated with the above reducing agent bath and the oxidizing agent solutions A and B at a temperature of 24° to 25° C.

The treatment with the reducing agent was effected for 15 min., and the oxidizing agent solution A was applied in the form of a shower to the hair. Three minutes after the commencement of the treatment with the oxidizing agent, the pH of the oxidizing agent bath shifted to 4.3, and after a further 2 min., it became 4.6, after which the pH was not changed. After the hair was treated with the oxidizing agent solution A for 10 min. in total, the oxidizing agent solution B was added to the oxidizing agent solution A, upon which the pH thereof became 4.2. The hair was further treated with the resulting mixture. When this treatment was effected for one minute, the pH of the mixture became 4.5. However, the pH was not changed thereafter. The treatment with the mixture was finished in 10 min., after which the hair was washed with water, dried and then finished.

The elevation of the pH is considered to result from elimination of waste matter from the hair and scalp, and as a result of the treatment, the white hair became yellowish, and the glowing beauty and gloss characteristic of white hair could not be obtained.

EXAMPLE 3

The same reducing agent bath and oxidizing agent solutions A and B as in Comparative Example 1 were prepared.

After 10 days from the treatment in Comparative Example 1, the white hair was treated again with the thus prepared reducing agent bath and oxidizing agent solutions A and B at 24°–25° C. while adjusting the pH's of the oxidizing agent solutions A and B as follows:

After the treatment with the reducing agent bath for 15 min., the oxidizing agent solution A was applied in the form of a shower to the hair. After 5 min. from the starting of this treatment, the pH of the oxidizing agent solution A was changed to 4.6. At this time, citric acid was added to the solution A to adjust the pH thereof to 4.3, and the treatment with the solution A was continued to effect the treatment for 10 min. in total. The oxidizing agent solution B was added thereto, upon which the pH of the resulting mixture became 3.8. The hair was treated with the resulting mixture. After three minutes, the pH of the mixture became 4.0, and the treatment was continued with the mixture as such. The treatment with the mixture containing the oxidizing agent solution B was effected for 10 min. in total, after which the hair was washed with water, dried and finished.

By the above treatment, the gloss of the hair was recovered and the hair became glowing white, and was softly finished.

Comparing Comparative Example 1 with Example 3, it can be seen that only when the pH of the oxidizing agent solution A is lower than the pH of the reducing agent bath and the pH of the oxidizing agent solution B is lower than the pH of the oxidizing agent solution A, a good result can be obtained.

EXAMPLES 4 TO 14 AND COMPARATIVE EXAMPLES 2 TO 14

Various hairs were treated with the following compositions with varying the pH values of the compositions as shown in Table 1 to obtain the results as shown in Table 1.

| (1) Reducing agent bath (first bath) | |
| --- | --- |
| Thioglycolic acid | 6.0 parts by weight |
| Glycerol | 5.0 parts by weight |
| Ammonia water (25% by weight) | 4.0 parts by weight |

These components were dissolved in water to make the total weight 100 parts by weight. The resulting solution had a pH of 4.0. To the solution was added ammonia water or citric acid to prepare a reducing agent bath having a pH adjusted as shown in Table 1.

| (2) Oxidizing agent bath (second bath) | | |
| --- | --- | --- |
| Sodium bromate | 6.0 | parts by weight |
| Glutamic acid | 0.7 | parts by weight |
| Nitric acid | 0.01 | parts by weight |

These components were dissolved in distilled water to make the total weight 200 parts by weight. The resulting aqueous solution had a pH of 3.5. To the solution was added ammonia water or citric acid to obtain an oxidizing agent bath having a pH adjusted as shown in Table 1.

The tests shown in Table 1 were effected by treating the hairs of six Japanese women (A) to (F) as explained below, the hair of each woman being divided into four sections (front, back, left and right), with combinations of the reducing agent bath and the oxidizing agent bath different in pH value under otherwise the same conditions (concentration, bath temperature, and treating time).

(A) Hair of woman 27 years old having an isoelectric point of 5.0, who has never been subjected to permanent wave treatment.

(B) Hair of woman 25 years old having an isoelectric point of 5.0 who has never been subjected to permanent wave treatment.

(C) Hair of woman 23 years old having an isoelectric point of 5.5 who had been subjected to a treatment with the present composition before two weeks and before one week, each one time.

(D) Hair of woman 37 years old having an isoelectric point of 6.0 which had been subjected to hair dyeing one time per two months and to conventional permanent wave treatment (using alkaline permanent waving solutions) one time per 1.5 months.

(E) Hair of woman 30 years old having an isoelectric point of 6.3 which had been subjected to conventional permanent wave treatment (using alkaline permanent waving solutions) one time per 2 months.

(F) Hair of woman 21 years old having an isoelectric point of 5.0 which had never been subjected to permanent wave treatment.

The hair samples were thoroughly cleansed to remove oils and other contaminations and dried. To the thus dried hair samples were applied the reducing agent solutions having the pH values shown in Table 1. The scalp was massaged for two minutes, after which the hair was rolled on curling rods (7 min.) and then allowed to stand for 8 min. Thus, it followed that the treatment with the reducing agent solution was effected for 17 min. in total. To the hair was thereafter applied the oxidizing agent solution A, and the hair was allowed to stand for 20 min., after which the oxidizing agent solution B was applied to the hair and the hair was allowed to stand for 20 min., washed with water, dried, and then observed to evaluate the results of test.

Table 1

| Example No. | pHi sample hair | pH of reducing agent bath[1] | pH of oxidizing agent Solution A[2] | pH of oxidizing agent Solution B[3] | Difference between pHi and pH of oxidizing agent bath | Test curl[5] | Wave state After-treatment with oxidizing agent bath[6] | Stability[7] |
|---|---|---|---|---|---|---|---|---|
| Example 4 | | 3.2 (−1.8) | 2.7 (−0.5) | 2.2 (−0.5) | −(2.3 − 2.8) | △ | ○ | ○ |
| Comparative Example 2 | (A) 5.0 | 3.2 | 3.2 (±0) | 3.2 (±0) | −(1.8 − 1.8) | △ | △ | × |
| Example 5 | | 4.5 (−0.5) | 4.0 (−0.5) | 3.5 (−0.5) | −(1.0 − 1.5) | ○ | ◎ | ◎ |
| Comparative Example 3 | | 4.5 | 6.6 (+2.1) | 6.9 (+0.3) | +(1.6 − 1.9) | ○ | △ | × |
| Example 6 | | 4.5 (−0.5) | 4.0 (−0.5) | 3.5 (−0.5) | −(1.0 − 1.5) | ○ | ◎ | ◎ |
| Comparative Example 4 | (B) 5.0 | 4.5 | 6.6 (+2.1) | 6.9 (+0.3) | +(1.6 − 1.9) | ○ | △ | × |
| Example 7 | | 4.9 (−0.1) | 4.6 (−0.3) | 4.3 (−0.3) | −(0.4 − 0.7) | ◎ | ◎ | ◎ |
| Comparative Example 5 | | 4.9 | 4.6 (−0.3) | 5.6 (+1.0) | −0.4 − +0.6 | ◎ | △ | × |
| Example 8 | | 4.3 (−1.2) | 3.8 (−0.5) | 3.3 (−0.5) | −(1.7 − 2.2) | ○ | ○ | ○ |
| Comparative Example 6 | (C) 5.5 | 4.3 | 7.6 (+3.3) | 7.9 (+0.3) | +(2.1 − 2.4) | ○ | △ | × |
| Example 9 | | 4.8 (−0.7) | 4.5 (−0.3) | 4.2 (−0.3) | −(1.0 − 1.3) | ◎ | ◎ | ◎ |
| Comparative Example 7 | | 4.8 | 3.8 (−1.0) | 2.8 (−1.0) | −(1.7 − 2.7) | ◎ | ○ | △ |
| Example 10 | | 4.0 (−2.0) | 3.5 (−0.5) | 3.0 (−0.5) | −(2.5 − 3.0) | △ | ○ | ○ |
| Comparative Example 8 | (D) 6.0 | 4.0 | 6.5 (+2.5) | 6.2 (−0.3) | +(0.5 − 0.2) | △ | △ | × |
| Example 11 | | 5.9 (−0.1) | 5.2 (−0.7) | 4.8 (−0.4) | −(0.8 − 1.2) | ◎ | ◎ | ◎ |
| Comparative Example 9 | | 5.9 | 6.5 (+0.6) | 6.2 (−0.3) | +(0.5 − 0.2) | ◎ | △ | × |
| Comparative Example 10 | | 4.0 (−2.3) | 3.5 (−0.5) | 3.0 (−0.5) | −(2.8 − 3.3) | △ | ○ | △ |
| Comparative Example 11 | (E) 6.3 | 4.0 | 6.5 (+2.5) | 6.2 (−0.3) | +0.2 − −0.1 | △ | ○ | × |
| Example 12 | | 5.5 (−0.8) | 5.2 (−0.3) | 4.8 (−0.4) | −(1.1 − 1.5) | ◎ | ◎ | ◎ |
| Comparative Example 12 | | 5.5 | 6.5 (+1.0) | 6.2 (−0.3) | +0.2 − −0.1 | ◎ | △ | × |
| Example 13 | | 3.7 (−1.3) | 3.2 (−0.5) | 2.7 (−0.5) Alkali[4] agent | −(1.8 − 2.3) | ○ | ○ | ○ |
| Comparative Example 13 | (F) 5.0 | 3.7 | 3.2 (−0.5) | −1.8 | | ○ | ○ | ○ |
| Example 14 | | 4.0 (−1.0) | 3.5 (−0.5) | 3.0 (−0.5) Alkali[4] agent | −(1.5 − 2.0) | ◎ | ◎ | ◎ |
| Comparative Example 14 | | 4.0 | 3.5 (−0.5) | −1.5 | | ○ | ○ | ○ |

Note:
[1] Figures in parentheses refer to difference between pHi and the pH of the reducing agent bath.
[2] Figures in parentheses refer to difference between pH of the reducing agent and pH of the oxidizing agent solution A.
[3] Figures in parentheses refer to difference between pH of the oxidizing agent solution A and pH of the oxidizing agent solution B.
[4] Treated with a 1% aqueous sodium carbonate solution free from the oxidizing agent.
[5] ×: No curl, △: Incompletely curled, ○: Fairly completely curled, ◎: Completely curled.
[6] ×: Wave disappeared substantially completely by rinsing, △: Very weak wave remained after rinsing, ○: Wave remained fairly completely after rinsing, ◎: Wave remained completely after rinsing.
[7] ×: Wave disappeared completely 2 days after the treatment, △: Wave nearly disappeared 2 days after the treatment, ○: Wave remained fairly completely 2 days after treatment, ◎: Wave not changed 2 days after the treatment (= stable).
[8] "pHi" refers to isolectric point.

Comparing Example 5 with Comparative Example 3, the test curl was good in Comparative Example 3, while wave nearly disappeared after the treatment with the oxidizing agent bath. In Example 5, the test curl was similarly good, but unlike Comparative Example 3, the wave remained substantially completely even after the treatment with the oxidizing agent bath. This is considered to be because in Example 5, the acidity of the oxidizing agent bath is stronger than that of the reducing agent bath, and hence the oxidizing agent bath has a great penetrating force, which favorably affected the stabilization of wave.

As is clear from the above data, the reducing agent bath is prepared so as to have a pH 0.1 to 2.0 lower, preferably 0.1 to 1.0 lower, than the isoelectric point of the hair, and the oxidizing agent bath is prepared so as to have a pH 0.1 to 2.0 lower than the pH of the reducing agent bath but not more than 3.0 lower than the isoelectric point of the hair, or alternatively, two oxidizing agent solutions A and B are prepared, the oxidizing agent solution A having a pH 0.1 to 1.5 lower than the pH of the reducing agent bath, and the oxidizing agent solution B having a pH 0.1 to 2.0 lower than the pH of the oxidizing agent solution A but not more than 3.0 lower than the isoelectric point of the hair. When the hair is treated with these treating solutions having a pH outside the above ranges, the treated hair is inferior to permanent wave effect, and when the scalp or other skins are treated therewith the effect on elimination of waste matter from the skins and the metabolic effect are greatly inferior to those of the present two-bath type composition.

EXAMPLE 15

[I] In order to compare the effect of the present acidic two-bath type composition on the strength of hair with that of the conventional alkaline permanent waving preparation and that of the composition of French Pat. No. 1,537,672, the following test was conducted.

(1) Conventional alkaline permanent-waving preparation (I)
  (a) Reducing agent solution
    Thioglycolic acid               6.3 parts by weight
    Ammonia water
    (25% by weight)                 8.0 parts by weight
    Potassium carbonate         0.5 parts by weight
    Emulsifier                        1 parts by weight
    Distilled water to make 100 parts by weight.
  The pH of the solution was 9.3.
  (b) Oxidizing agent solution
    Sodium bromate               4 parts by weight
    Distilled water to make 100 parts by weight.
(2) The present acidic two-bath type composition (II)
  (a) Reducing agent solution
    Thioglycolic acid               6.0 parts by weight
    Ammonia water
    (25% by weight)                 4.0 parts by weight
    Glycerol                         5.0 parts by weight
    Distilled water to make 100 parts by weight.
  The resulting solution had a pH of 4.0.
  (b) Oxidizing agent solution
    Sodium bromate               8.0 parts by weight
    Glutamic acid                 0.7 part by weight
    Nitric acid                      0.02 part by weight
    Distilled water to make 100 parts by weight.
  The resulting solution had a pH of 3.5.
(3) After-treating alkali solution (III) (according to French Patent 1,537,672)
    10 % aqueous sodium
    carbonate solution            200 parts by weight The test was effected at 21° C. at a relative humidity of 80% on sample hair which had been immersed in the reducing agent solution, thereafter in the oxidizing agent solution, and if necessary, in the after-treating alkali solution, and well washed with water and dried. One piece of the sample hair was loaded with a weight and drawn while gradually increasing the weight. When the hair was cut, the length (b cm) of the hair at that time and the weight (c g) at that time were determined. From these values, the initial length (a cm) of the hair and the thickness (dμ) of the hair, the elongation and strength were calculated according to the following equations:

$$\text{Elongation} = \frac{b - a}{a} \times 100\ (\%)$$
$$\text{Strength} = [c/\pi\ (d/2)^2] \times 100$$

The thickness (d) was measured by means of a microscale.

Hair samples (G, H, I) were taken from the hair of three Japanese women, and treated with the above-mentioned treating solutions under the conditions shown in Table 2.

Table 2

| Run No. | Hair sample Kind | pHi | Treating bath | Treating time (min.) Reducing | Oxidizing | Alkali after-treating |
|---|---|---|---|---|---|---|
| 1-1 | (G) | 5.2 | None | — | — | — |
| 1-2 | " | " | (II) | 7 | 15 | — |
| 1-3 | " | " | (II) – (III) | 7 | 15 | 5 |
| 1-4 | " | " | (I) | 8 | 15 | — |
| 2-1 | (H) | 5.6 | None | — | — | — |
| 2-2 | " | " | (II) | 5 | 15 | — |
| 2-3 | " | " | (II) – (III) | 5 | 15 | 5 |
| 2-4 | " | " | (I) | 8 | 15 | — |
| 3-1 | (I) | 5.9 | None | — | — | — |
| 3-2 | " | " | (II) | 10 | 15 | — |
| 3-3 | " | " | (II) – (III) | 10 | 15 | 5 |
| 3-4 | " | " | (I) | 15 | 20 | — |

The test was conducted on 10 pieces of hair. The elongation and strength obtained were as shown in Table 3.

Table 3

| Run No. | Thickness (μ) | Cross-sectional area (μ²) | Tension (g) | Elongation (%) |
|---|---|---|---|---|
| 1-1 | 90.4 | 6415 | 139.2 | 68.5 |
| 1-2 | 86.0 | 5806 | 106.3 | 67.5 |
| 1-3 | 87.1 | 6264 | 125.2 | 69.5 |
| 1-4 | 92.7 | 6760 | 139.3 | 77.4 |
| 2-1 | 78.0 | 4776 | 108.0 | 62.4 |
| 2-2 | 75.8 | 4498 | 84.6 | 58.8 |
| 2-3 | 76.2 | 4561 | 98.7 | 64.3 |
| 2-4 | 77.0 | 4653 | 96.3 | 68.0 |
| 3-1 | 82.5 | 5357 | 123.0 | 71.9 |
| 3-2 | 74.4 | 4346 | 106.8 | 71.1 |
| 3-3 | 75.3 | 4462 | 93.0 | 68.6 |
| 3-4 | 88.0 | 6079 | 120.2 | 66.6 | elongation of hair treated with the acidic two-bath type composition decreases as compared with that of untreated hair, while in the case of treatment with the conventional alkaline permanent-waving preparation and treatment with the acidic two-bath type composition plus after-treatment with alkali solution, the elongation increases as compared with that of untreated hair, except Run Nos. 3-1 to 3-4.

[II] Measurement of wave percentage

The hair of a Japanese woman having an isoelectric point of 5.1 and a thickness of 80–90 μ (hair sample (J) was treated with the precent acidic two-bath type composition [(a) reducing agent solution and (b) oxidizing agent solution] while varying the pH of (a) and (b) with ammonia water, potassium carbonate or citric acid, and the wave percentage of the treated hair was determined in the following manner:

A piece of hair sample was wound in parallel, i.e., without crossing, in several coils on a glass tube having an outer diameter of 8 mm under a load of 3 g while fixing one end of the hair sample on a protrusion on the glass tube, and the other end of the hair was then fixed on another protrusion on the glass tube so that the hair did not move. The hair wound on the glass tube as such was immersed in the reducing agent solution (a) for 15 min., and then in the oxidizing agent solution (b) for 20 min., and then washed with water. The hair was cut with a knife in parallel to the axis of the glass tube to obtain several cut circles of hair. These cut circles of hair were placed in a petri dish filled with water, and the diameter of the circle made by the cut hair was measured. The wave percentage was determined by dividing the outer diameter of the glass tube by the diameter of the circle made by the cut hair as follows:

$$\text{Wave percentage (\%)} = \frac{\text{Outer diameter of glass tube}}{\text{Diameter of circle made by cut hair}} \times 100$$

In each test, 10 pieces of hair were used, and 5 pieces thereof was subjected to measurement of diameter immediately after the treatment, while the remaining 5 pieces were removed from the glass tube without cutting after the treatment, and after two days they were again wound on the glass tube in the same manner, and cut in the same manner as above, after which the diameter of the circle made by the cut hair was measured to obtain the wave percentage. The results obtained were as shown in Table 4, in which the ratio of the wave percentage immediately after the treatment to the wave percentage 2 days after the treatment is also shown.

| (a) Reducing agent solution (first bath) | |
|---|---|
| Thioglycolic acid | 6.0 parts by weight |
| Ammonia water (25% by weight) | 8.0 parts by weight |
| Glycerol | 5.0 parts by weight |
| Distilled water to make 100 parts by weight. | |

These components were mixed to prepare an aqueous solution, and the pH of the solution was adjusted to a value as shown in Table 5 by adding thereto ammonia water or citric acid.

| (b) Oxidizing agent solution A (second A bath) | |
|---|---|
| Sodium bromate | 6.0 parts by weight |
| Glutamic acid | 0.7 parts by weight |
| Nitric acid | 0.01 parts by weight |
| Distilled water to make 200 parts by weight. | |

These components were mixed to prepare an aqueous solution, and the pH thereof was adjusted to a value as shown in Table 5 by adding thereto ammonia water or citric acid.

| (c) Oxidizing agent solution B (second B bath) | |
|---|---|
| Sodium bromate | 10.0 parts by weight |
| Glutamic acid | 0.7 parts by weight |
| Nitric acid | 0.02 parts by weight |
| Distilled water to make 200 parts by weight. | |

Table 4

| Run No. | pHi of hair Sample (J) | pH of reducing agent solution[1] | pH of oxidizing agent solution[2] | Difference between pHi and pH of oxidizing agent solution | Wave percentage[3] Immediately after treatment (e) (%) | 2 Days after treatment (f) (%) | (f)/(e) × 100 (%) |
|---|---|---|---|---|---|---|---|
| 4-1 | | 4.0 (−1.1) | 3.5 (−0.5) | −1.6 | 67.2 | 63.0 | 93.8 |
| 4-2 | | 4.0 | 2.5 (−1.5) | −2.6 | 56.3 | 50.6 | 90.0 |
| 4-3 | | 4.0 | 5.0 (+1.0) | −0.1 | 53.3 | — | — |
| 5-1 | | 4.5 (−0.6) | 4.0 (−0.5) | −1.1 | 70.1 | 69.6 | 99.3 |
| 5-2 | 5.1 | 4.5 | 5.0 (+0.5) | −0.1 | 53.0 | — | — |
| 5-3 | | 4.5 | 2.5 (−2.0) | −2.6 | 60.6 | 57.1 | 94.2 |
| 6-1 | | 5.0 (−0.1) | 4.5 (−0.5) | −0.6 | 72.1 | 69.6 | 94.2 |
| 6-2 | | 5.0 | 5.6 (+0.6) | +0.5 | 54.1 | — | — |
| 6-3 | | 5.0 | 3.0 (−2.0) | −2.1 | 61.1 | 56.0 | 91.6 |

Note:
[1]Figures in parentheses refer to difference between pHi and pH of the reducing agent solution.
[2]Figures in parentheses refer to difference between pH of the reducing agent solution and pH of the oxidizing agent solution.
[3]"—" refers to measurement of diameter of circle made by cut hair having been impossible because wave disappeared.

[III] Use of oxidizing agent solutions A and B

The same hair sample as in above [II] was treated with the following treating solutions in the same manner as in above [II], and then subjected to the same test as in above [II] to obtain the results shown in Table 5.

These components were mixed to prepare an aqueous solution, and the pH thereof was adjusted to a value as shown in Table 5 by adding thereto ammonia water or citric acid.

Table 5

| Run No. | pHi of hair sample | pH of reducing agent solution[1] | pH of oxidizing agent solution A[2] | pH of oxidizing agent solution B[3] | Difference between pHi and pH of the oxidizing agent bath | Wage percentage Immediately after treatment (e) (%) | 2 days after treatment (f) (%) | (f)/(e) × 100 (%) |
|---|---|---|---|---|---|---|---|---|
| 7-1 | | 3.5 (−1.6) | 3.3 (−0.2) | 3.1 (−0.2) | −(1.8 - 2.0) | 64.5 | 61.5 | 95.2 |
| 7-2 | | 3.5 | 4.5 (+1.0) | 5.0 (+0.5) | −(0.6 - 0.1) | 55.9 | 44.0 | 78.1 |
| 7-3 | | 3.5 | 2.8 (−0.7) | 2.2 (−0.6) | −(2.3 - 2.9) | 60.6 | 50.0 | 82.5 |
| 8-1 | | 4.0 (−1.1) | 3.5 (−0.5) | 3.2 (−0.3) | −(1.6 - 1.9) | 69.6 | 68.4 | 98.3 |
| 8-2 | 5.1 | 4.0 | 4.5 (+0.5) | 5.0 (+0.5) | −(0.6 - 0.1) | 57.1 | 44.1 | 77.2 |
| 8-3 | | 4.0 | 3.0 (−1.0) | 2.2 (−0.8) | −(2.1 - 2.9) | 58.0 | 49.7 | 84.0 |
| 9-1 | 4.5 (−0.6) | 4.0 (−0.5) | 3.5 (−0.5) | −(1.1 - 1.6) | 72.7 | 70.8 | 97.4 |
| 9-2 | | 4.5 | 5.0 (+0.5) | 5.7 (+0.7) | −0.1 - +0.6 | 56.3 | 46.2 | 82.1 |
| 9-3 | | 4.5 | 3.0 (−1.5) | 2.3 (−0.7) | −(2.1 - 2.8) | 62.0 | 59.3 | 95.6 |
| 10-1 | | 5.0 (−0.1) | 4.5 (−0.5) | 4.0 (−0.5) | −(0.6 - 1.1) | 76.2 | 75.5 | 99.0 |
| 10-2 | 5.1 | 5.0 | 5.6 (+0.6) | 6.2 (+0.6) | +(0.5 - 1.1) | 57.1 | 47.0 | 81.3 |

Table 5-continued

| Run No. | pHi of hair sample | pH of reducing agent solution[1] | pH of oxidizing agent solution A[2] | pH of oxidizing agent solution B[3] | Difference between pHi and pH of the oxidizing agent bath | Wage percentage Immediately after treatment (e) (%) | Wage percentage 2 days after treatment (f) (%) | (f)/(e) × 100 (%) |
|---|---|---|---|---|---|---|---|---|
| 10-3 | 5.0 | 3.0 (−2.0) | 2.5 (−0.5) | −(2.1 − 2.6) | 67.2 | 64.0 | 95.2 |

Note:
[1] Figures in parentheses refer to difference between pHi and pH of the reducing agent solution.
[2] Figures in parentheses refer to difference between pH of the reducing agent solution and pH of the oxidizing agent solution A.
[3] Figures in parentheses refer to difference between pH of the oxidizing agent solution A and pH of the oxidizing agent solution B.

In Table 4 (combination of a reducing agent solution with an oxidizing agent solution) and Table 5 (combination of a reducing agent with two oxidizing agent solutions A and B), the comparison between the hair samples treated with the treating solutions satisfying the conditions of the present invention indicates that the waving effect in Table 5 is slightly higher than in Table 4, but there is no essential difference therebetween. It can be seen, therefore, that concerning permanent-waving, the treatment with the reducing agent solution and one oxidizing agent solution, that is, without treating with the oxidizing agent solution B, yields a sufficiently satisfactory waving effect. However, in order to achieve more sufficient oxidizing effect and accelerate the metabolism of the scalp and other skins, it can be seen that the use of the two oxidizing agent solutions A and B is preferable.

What is claimed is:

1. A process for treating human hair and scalp, which comprises applying to the hair and scalp an aqueous reducing agent solution containing 3 to 10% by weight of at least one mercaptan acid and having a pH adjusted with a base to a value 0.1 to 2.0 lower than the isoelectric point of the hair or scalp; allowing the thus treated hair and scalp to stand for a period of 10 to 30 minutes while substantially protecting the hair and scalp from air, applying to the thus treated hair and scalp an aqueous oxidizing agent solution (A) containing 0.5 to 3 percent by weight of sodium bromate, potassium bromate, or hydrogen peroxide and having a pH 0.1 to 1.5 lower than the pH of the reducing agent solution but not more than 3.0 lower than the isoelectric point of the hair or scalp for 10 to 15 minutes; and then applying to the hair and scalp an aqueous oxidizing agent solution (B) containing 1 to 5 percent by weight of sodium bromate, potassium bromate or hydrogen peroxide and having a pH 0.1 to 2.0 lower than the pH of the aqueous oxidizing agent solution (A) but not more than 3.0 lower than the isoelectric point of the hair or scalp for a period of 10 to 30 minutes, thereafter wash said hair and scalp with water and drying.

2. The process of claim 1, wherein immediately after the application of said aqueous reducing agent solution, the treated hair is wound on curling rods, and then treated with said aqueous oxidizing agent solutions (A) and (B), after which the curling rods are removed to impart permanent wave to the hair.

3. The process of claim 1, wherein the temperature of said aqueous reducing agent solution is 20° to 40° C. and the temperature of the aqueous oxidizing agent solutions (A) and (B) is 20° to 40° C.

4. The process of claim 1, wherein the total quantity of said aqueous oxidizing agent solutions (A) and (B) applied to said hair and scalp is two to three times the quantity of said aqueous reducing agent solution which has been applied to said hair and scalp.

5. The process of claim 1, wherein said oxidizing agent solution A has a pH 0.3 to 0.5 lower than the pH of said reducing agent solution and said oxidizing agent solution B has a pH of 0.3 to 0.5 lower than the pH of said oxidizing agent solution A.

* * * * *